United States Patent [19]

Kammann, Jr. et al.

[11] Patent Number: 5,080,813
[45] Date of Patent: Jan. 14, 1992

[54] LUBRICANT COMPOSITION CONTAINING DIALKYLDITHIOPHOSPHORIC ACID NEUTRALIZED WITH ALKOXYLATED ALIPHATIC AMINES

[75] Inventors: Karl P. Kammann, Jr., Crown Pt.; William R. Garrett, Schereville, both of Ind.

[73] Assignee: Ferro Corporation, Cleveland, Ohio

[21] Appl. No.: 498,554

[22] Filed: Mar. 26, 1990

[51] Int. Cl.$^5$ .......................................... C10M 137/08
[52] U.S. Cl. .............................. 252/32.7 R; 558/207; 558/208; 72/42
[58] Field of Search ............ 252/32.7 E, 49.5, 32.7 R; 558/208, 207

[56] References Cited

U.S. PATENT DOCUMENTS

| | | | |
|---|---|---|---|
| 3,496,152 | 2/1970 | Morita | 558/208 |
| 4,019,991 | 4/1977 | Jayne | 252/48.2 |
| 4,416,667 | 11/1983 | Kaufman et al. | 558/207 |
| 4,575,431 | 3/1986 | Salentine | 252/32.7 E |
| 4,721,802 | 1/1988 | Forsberg | 558/207 |
| 4,772,739 | 9/1988 | Forsberg | 558/208 |
| 4,774,351 | 9/1988 | Forsberg | 558/207 |

FOREIGN PATENT DOCUMENTS 116399 10/1984 European Pat. Off. .

Primary Examiner—Prince Willis, Jr.
Assistant Examiner—Ellen McAvoy
Attorney, Agent, or Firm—Daniel J. Hudak Co.

[57] ABSTRACT

Amine salts having utility in metalworking operations is disclosed. The amine salts are prepared by the reaction of (A) a dihydrocarbyldithiophosphoric acid of the formula

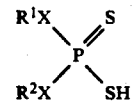

wherein $R^1$ and $R^2$ are hydrocarbyl-based groups independently containing from about 5 to about 30 carbon atoms, X is oxygen or sulfur, and (B) an alkoxylated amine prepared by reacting a nontertiary amine comprising
  (a) a monoamine,
  (b) a diamine, or
  (c) a polyamine,
with from about 2 up to about 15 moles of an alkylene oxide comprising ethylene oxide or propylene oxide.

19 Claims, No Drawings

LUBRICANT COMPOSITION CONTAINING DIALKYLDITHIOPHOSPHORIC ACID NEUTRALIZED WITH ALKOXYLATED ALIPHATIC AMINES

FIELD OF INVENTION

This invention relates to metal working additives. More particularly, it relates to additives useful as lubricants during metal working operations and to methods for lubricating metal during such operations.

Metal working operations, for example rolling, forging, hot pressing, blanking, bending, stamping, drawing, cutting, punching, spinning, and the like, generally employ a lubricant to facilitate the same. Lubricants greatly improve these operations in that they can reduce the power required for the operation, prevent sticking, and decrease wear of dies, cutting bits, and the like. Additionally, the lubricants frequently provide rust-inhibiting properties to the metal being treated.

BACKGROUND ART

The utilization of water-based metal working lubricants and coolants has become well established in light to medium-duty applications such as cutting and grinding. Such fluids not only remove heat, but also serve to inhibit corrosion, lubricate, reduce surface tension, provide extreme pressure lubrication, and control bacterial growth.

In the past, oil-based lubricant additives in most cases provided suitable anti-wear and extreme pressure performance by the use of chlorinated paraffins or waxes in their formulations. However, with increasing environmental demands, relating both to use and disposal, emphasis has been placed on the use of water-based fluids thus minimizing the presence of mineral oils and minimizing the use of chlorinated hydrocarbons.

U.S. Pat. No. 4,575,431 (Salentine, Mar. 11, 1986), relates to extreme pressure additives for lubricating oils. More particularly, the reference relates to the finding that the extreme pressure properties of a lubricant are greatly improved by the addition of a specific mixture of phosphates, said phosphates comprising: (a) substituted dithiophosphates, and (b) mono and di-substituted sulfur-free phosphates wherein the composition has been neutralized by reaction with a hydrocarbyl amine.

European Patent Application 116,399 (Forsberg, U.S. Ser. No. 456,219; filed Jan. 7, 1983), relates to phosphorus, sulfur, and nitrogen-containing salts prepared from dithiophosphorus compounds and polyamines, which salts are characterized by their anti-wear and extreme pressure properties. More particularly, the reference relates to novel phosphorus, sulfur, and nitrogen-containing salts prepared from dithiophosphorus acids selected from the group consisting of dithiophosphoric, dithiophosphinic, and dithiophosphonic acid compounds and polyamines. This reference further relates to aqueous compositions for use as functional fluids for use in hydraulic and metal cutting applications comprising a continuous aqueous phase, a dithiophosphorus acid/amine salt, and optionally a surfaceactive agent.

SUMMARY OF THE INVENTION

This invention is directed to an additive composition having utility in metal working formulations. The additive composition is a salt prepared by reacting (A) a dihydrocarbyldithiophosphoric acid of the formula

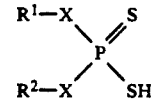

wherein $R^1$ and $R^2$ are each independently hydrocarbyl groups of from about 5 up to about 30 carbon atoms and X is oxygen or sulfur with (B) an alkoxylated amine prepared by reacting a non-tertiary amine with ethylene oxide or propylene oxide.

DETAILED DESCRIPTION

The amine salt of a dihydrocarbyldithiophosphoric acid with an alkoxylated amine is prepared by neutralizing (A) a dihydrocarbyldithiophosphoric acid with (B) an alkoxylated amine.

Reactant (A): The Dihydrocarbyldithiophosohoric Acid

The dihydrocarbyldithiophosphoric acids which are included in the compositions of the present invention are characterized by the formula $$\begin{array}{c} R^1-X \\ \phantom{R^1-X}\diagdown \phantom{X}S \\ \phantom{R^1-XXXX}P \\ \phantom{R^1-X}\diagup \phantom{X}\diagdown \\ R^2-X \phantom{XXX} SH \end{array}$$

wherein $R^1$ and $R^2$ are hydrocarbyl-based groups. The hydrocarbyl groups $R^1$ and $R^2$ each independently contain from about 5 up to about 30 carbon atoms, preferably from about 5 to about 22, and most preferably from about 6 to about 18 carbon atoms. Within this invention, X is either sulfur or oxygen; preferably X is oxygen.

As used in this specification and appended claims, the terms "hydrocarbyl" or "hydrocarbon-based" denote a group having a carbon atom directly attached to the remainder of the molecule and having predominantly hydrocarbon character within the context of this invention. Such groups include the following:

(1) Hydrocarbon groups; that is, aliphatic (e.g., alkyl or alkenyl) and alicyclic (e.g., cycloalkyl or cycloalkenyl), and the like, as well as cyclic groups wherein the ring is completed through another portion of the molecule (that is, any two indicated substituents may together form ar alicyclic group). Such groups are known to those skilled in the art. Examples include amyl, hexyl, 2-ethylhexyl, octyl, nonyl, decyl, lauryl, cetyl, octadecyl, cyclohexyl, etc.

(2) Substituted hydrocarbon groups; that is, groups containing non-hydrocarbon substituents which, in the context of this invention, do not alter the predominantly hydrocarbon character of the group. Those skilled in the art will be aware of suitable substituents. Examples include hydroxy, nitro, cyano, alkoxy, acyl, etc.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen, and sulfur.

In general, no more than about three substituents or hetero atoms, preferably no more than one, and most preferably no hetero atoms will be present for each 10 carbon atoms in the hydrocarbyl group.

Terms such as "alkyl-based group" and the like have meaning analogous to the above with respect to alkyl groups and the like.

When X is oxygen, the $R^1$ and $R^2$ groups may comprise a mixture of hydrocarbyl groups derived from commercial alcohols. Examples of some preferred monohydric alcohols and alcohol mixtures include the commercially available "Alfol" alcohols marketed by the Du Pont Company. Alfol 810 is a mixture containing alcohols consisting essentially of straight-chain, primary alcohols having 8 and 10 carbon atoms. Alfol 12 is a mixture comprising mostly C12 fatty alcohols. Alfol 1218 is a mixture of synthetic, primary, straight-chain alcohols having an even number of carbon atoms of from about 12 to about 18. The Alfol 20+ alcohols are mostly on an alcohol basis, C20 alcohols as determined by GLC (gas-liquid-chromatography).

Another example of a commercially available alcohol is Adol 60 which comprises about 75 percent by weight of a straight-chain C22 primary alcohol, about 15 percent of a C20 primary alcohol and about 8 percent of a C18 and C24 alcohols. Adol 320 comprises predominantly oleyl alcohol. The Adol alcohols are marketed by Sherex Chemical Company.

A variety of mixtures of monohydric fatty alcohols derived from naturally occurring triglycerides and ranging in chain length of from C8 to C18 are available from Procter and Gamble Company. These mixtures contain various amounts of fatty alcohols containing mainly 12, 14, 16, or 18 carbon atoms. For Example, CO-1214 is a fatty alcohol mixture containing 0.5 percent of C10 alcohol, 66.0 percent of C12 alcohol, 26.0 percent of C14 alcohol, and 6.5 percent of C16 alcohol.

Another group of commercially available mixtures include the "Neodol" products available from Shell Chemical Company. For example, Neodol 23 is a mixture of C12 and C13 alcohols; Neodol 25 is a mixture of C12 to C15 alcohols; Neodol 45 is a mixture of C14 to C15 linear alcohols. Neodol 91 is a mixture of C9, C10, and C11 alcohols.

When X is sulfur, the $R^1$ and $R^2$ groups may comprise a mixture of hydrocarbyl groups derived from mercaptans. Examples of some preferred mercaptans include octyl mercaptan, decyl mercaptan, and t-dodecyl mercaptan.

The dihydrocarbyldithiophosphoric acids (A) useful in the present invention may be prepared by techniques well known in the art. In one method of preparation, a primary alcohol or mixture of alcohols comprising straight-chain alcohols, branched-chain alcohols, or mixtures thereof, are reacted with phosphorus pentasulfide, $P_2S_5$, or homolog thereof (e.g., $P_4S_{10}$).

An example of this type of reaction is the reaction of phosphorus pentasulfide with octyl alcohol to produce O,O-di(octyl)dithiophosphoric acid according to the following equation:

$$4ROH + P_2S_5 \rightarrow 2(RO)_2\text{---PSSH} + H_2S.$$

In carrying out the above equation, a slight excess of alcohol is usually employed, such as 4.09 mole alcohol to 1 mole $P_2S_5$. The reaction temperatures range from about 50° C. up to about 200° C. The below example typifies the preparation of reactant (A).

EXAMPLE A-1

To a vessel fitted with a stirrer, nitrogen sparger, and an outlet leading to a Dean Stark trap below a water condenser, was added 211.7 grams of 2-ethylhexyl alcohol. The contents were heated to about 68° C. and 88.3 grams $P_2S_5$ was added in 13 increments. The reaction was exothermic and $P_2S_5$ was added at about every 20 minutes with the final increment raising the temperature to 105° C. After reaction of the last increment, the temperature was increased to 120° C. and held for 2 hours while blowing lightly with nitrogen below the surface to remove any residual $H_2S$. The contents were cooled to room temperature and filtered to give a clear product. The product had an acid value of 153 which corresponds to a found molecular weight of 367 versus a theoretical molecular weight of 355. The found molecular weight is determined by dividing 56,100 by the acid value. Elemental analysis of found/theoretical follows: % sulfur 17.1/18.1; % phosphorus 9.3/8.8.

Table I summarizes other alcohols utilized to prepare reactant (A) of the present invention.

TABLE I

| | Preparation of Dihydrocarbyldithiophosphoric Acids | | | | |
|---|---|---|---|---|---|
| EXAMPLE | ALCOHOL | MOLE RATIO ROH:P$_2$S$_5$ | ACID VALUE FOUND/THEORY | % S FOUND/THEORY | % P FOUND/THEORY |
| A-2 | n-octyl | 4.09:1 | 153/158 | 17.5/18.1 | 9.0/8.8 |
| A-3 | tridecyl | 4.30:1 | 108/113 | 12.3/13.0 | 5.8/6.3 |
| A-4 | isostearyl | 4.09:1 | 82/88 | /10.1 | /4.9 |
| A-5 | n-hexyl | 4.09:1 | 170/188 | 19.9/21.5 | 10.0/10.4 |
| A-6 | decyl | 4.09:1 | /136 | /15.6 | /7.6 |
| A-7 | oleyl | 4.09:1 | /89 | /10.2 | /4.9 |
| A-8 | 50% w n-octyl 50% w oleyl | 4.09:1 | /113 | /13.0 | /6.3 |

Reactant (B) The Alkoxylated Amine

The alkoxylated amine is prepared by reacting a nontertiary amine with an alkylene oxide. The nontertiary amine is (a) a monoamine, (b) a diamine, or (c) a polyamine.

(a) The Monoamine

The monoamine having utility in this invention is of the formula $R^3R^4NH$ wherein $R^3$ is a hydrocarbyl group containing from about 8 to about 22 carbon atoms and preferably from about 12 to about 18 carbon atoms. $R^3$ is aliptatic, that is alkyl or alkenyl and straight-chain or branched-chain. Within an alkenyl group, there are present one or two double bonds.

The alkyl group of the monoamine may also contain a hetero atom of oxygen or sulfur as in the formula $R^7\text{---}(OR^6)_b\text{NH}_2$ or $R^7\text{---}(SR^6)_b\text{NH}_2$ wherein $R^7$ is an alkyl group containing from 9 to about 15 carbon atoms, $R^6$ comprises $-CH_2-$, $-CH_2CH_2-$ or $-CH_2CH_2CH_2-$ and b is an integer of from 1 to about 3.

R⁴ is hydrogen or a hydrocarbyl group. As a hydrocarbyl group, R⁴ is aliphatic containing from 1 to about 4 carbon atoms. Preferably R⁴ is hydrogen.

Useful monoamines when R⁴ is hydrogen are octyl amine, nonyl amine, decyl amine, dodecyl amine, tridecyl amine, pentadecyl amine, and stearyl amine.

(b) The Diamine

A useful diamine within the purview of the invention is of the formula $H_2NR^5NH_2$ wherein $R^5$ is a hydrocarbylene group. The hydrocarbylene group $R^5$ is alkylene containing from 2 to about 22 carbon atoms and preferably from about 2 to about 10 carbon atoms. Illustrative of these diamines are ethylene diamine, 1,3-diamino propane, 1,4-diaminobutane, 1,5-diaminopentane, 1,6-diaminohexane, 1,8-diaminooctane, and 1,10-diaminodecane.

Another diamine having utility in this invention is of the formula

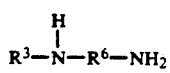

wherein $R^3$ and $R^6$ are as defined above. Preferably $R^3$ is a mixture of hydrocarbyl groups of from about 8 carbon atoms up to about 22 carbon atoms and identified as "Duomeens" available from Akzo Corporation. Duomeen C, Duomeen T, Duomeen S, and Duomeen 18 have an $R^3$ of coco, tallow, soya, and octadecyl and $R^6$ is —$CH_2CH_2CH_2$—.

(c) The Polyamine

Polyamines having utility in this invention are of the formula

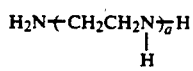

wherein a is an integer of from about 2 to about 10 and preferably from about 2 to about 5. The following are illustrative of the polyamines when a=2- diethylenetriamine; a=3- triethylenetetramine; a=4- tetraethylenepentamine; and a=5- pentaethylenehexamine.

Any of the above-described amines can be alkoxylated by reacting the amine with an alkylene oxide comprising ethylene oxide or propylene oxide. Preferred is ethylene oxide. The below equations show the formation of alkoxylated monoamines:

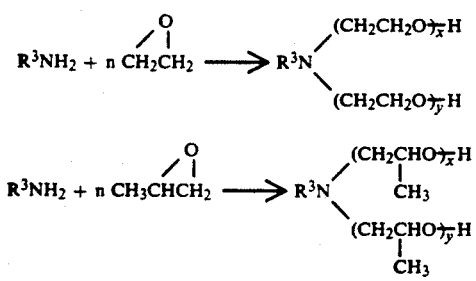

The number of moles of ethylene oxide is signified by "n." The ethylene oxide units range from about 2 to about 18 and preferably from about 5 to about 15. Within the above equation, n=x+y.

Useful ethoxylated monoamines are available from Sherex Chemicals. For example, Varonic® T205 is tallow amine ethoxylated with 5 moles ethylene oxide; Varonic® T210 is tallow amine ethoxylated with 10 moles ethylene oxide and Varonic® T215 is tallow amine ethoxylated with 15 moles ethylene oxide.

Ethoxylated monoamines are also available from Akzo Corporation. The number in parenthesis indicates the number of moles of ethylene oxide: Ethomeen C/15 -ethoxylated (5) cocoalkylamine, Ethomeen C/20, ethoxylated (10) cocoalkylamine, and Ethomeen C/25- ethoxylated (15) cocoalkylamine. The cocoalkyl group can be replaced with tallowalkyl, soyaalkyl or octadecyl groups.

Propoxylated monoamines are available from Akzo Corporation as Propomeen C/12 and Propomeen T/12 which respectively are N-cocoalkyl-1,1'iminobis-2-propanal and N-tallowalkyl-1,1'-iminobis-2-propanol.

Other monoamines that can be alkyoxylated with n moles of ethylene oxide are the ethoxyalkylamines of the formula $R^3(OR^6)_bNH_2$. These ethoxylated amines are available from Exxon's Tomah Products wherein $R^3$ is decyl, $R^6$ is —$CH_2CH_2CH_2$—, b is 1 and n is from about 5 to about 15.

Diamines that are alkoxylated are either of the formula $H_2NR^5NH_2$ or $R^3NHR^6NH_2$. An ethoxylated diamine of the latter formula is available from Akzo Corporation wherein $R^3$ is tallow and $R^6$ is —$CH_2CH_2CH_2$—. Their tradenames are Ethoduomeen T/20-ethoxylated (10) N-tallow-1,3-diaminopropane and Ethoduomeen T/25, ethoxylated (15) N-tallow-1,3-diamino-propane. The number in parentheses denotes the number of moles of ethylene oxide incorporated into the diamine. These ethoxylated Akzo diamines have the formula

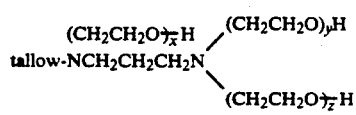

wherein n = x + y + z

Formation of the Product of (A) and (B)

The amine salt of the present invention is formed by the reaction or neutralization of reactant (A), the dihydrocarbyldithiophosphoric acid with reactant (B), the alkoxylated amine according to the below equation:

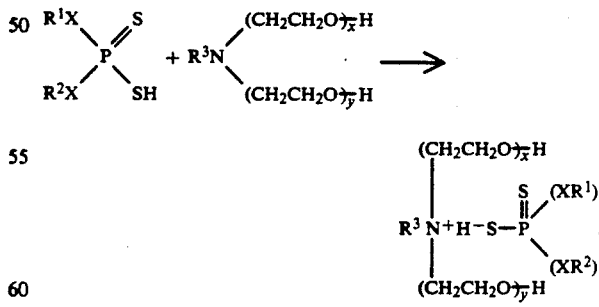

The amine salt compositions of this invention are prepared by reacting reactant (A) with reactant (B). The equivalent ratio of A:B is from about 1:1.01–1.12, preferably from about 1:1.01–1.07, and most preferably from about 1:1.01–1.03. The equivalents of reactants (A) and (B) are determined by their respective acid values and base values. Reactant (A) is added to reactant (B)

with stirring beginning at room temperature. The addition of reactant (A) is such that the resultant exotherm does not carry the temperature above 150° C.

The following examples illustrate the preparation of the amine salt compositions of the present invention, it being understood that this is merely intended to be illustrative and not limiting.

EXAMPLE 1

Added to a 5-liter, 4-necked, round-bottom flask fitted with a stirrer, thermowell, air condenser and addition funnel, was 1100 grams (3.0 equivalents) of Reactant (A) of Example A-2. The contents were stirred and beginning at room temperature 1452 grams (3.03 equivalents) ethoxylated tallowamine of the formula $$\text{"tallow-N}\begin{array}{c}(CH_2CH_2)_xH\\(CH_2CH_2)_yH\end{array} \quad \text{" to tallow-N}\begin{array}{c}(CH_2CH_2O)_xH\\(CH_2CH_2O)_yH\end{array}$$

available from Exxon's Tomah Products as Product E-T-5 was added from the addition funnel. The addition of the ethoxylated amine was exothermic and the addition was at a rate such that the resulting exotherm did not go beyond 75° C. Stirring was maintained for about 30 minutes and the liquid was the desired amine salt product containing 7.5 percent sulfur, 3.9 percent phosphorous and having an acid value of 65.

EXAMPLE 2

Employing the same equipment, temperature conditions, and techniques of Example 1, an amine salt was prepared using 1320 grams (4.0 equivalents) Reactant (A) of Example A-5 and 1233 grams (4.06 equivalents) of an ethoxylated amine of the formula $$\text{isodecyl-O}-(CH_2)_3N\begin{array}{c}CH_2CH_2OH\\CH_2CH_2OH\end{array}$$

available from Exxon's Tomah Products as Product E-14-2. The resulting product contained 10.5 percent sulfur, 5.4 percent phosphorous and had an acid value of 83.

EXAMPLE 3

Employing the same equipment, temperature conditions, and techniques of Example 1, an amine salt was prepared using 1559 grams (3 equivalents) Reactant (A) of Example A-3 and 1462 grams (3.05 equivalents) of the ethoxylated amine of Example 1. The resulting product contained 6.2 percent sulfur, 2.9 percent phosphorus and had an acid value of 56.

EXAMPLE 4

Employing the same equipment, temperature conditions, and techniques of Example 1, an amine salt was prepared using 1368 grams (2 equivalents) Reactant (A) of Example A-4 and 1913 grams (2.11 equivalents) of an ethoxylated amine of the formula $$\text{tallow-N}\begin{array}{c}(CH_2CH_2O)_xH\\(CH_2CH_2O)_yH\end{array}$$

wherein x+y=15, available from Exxon's Tomah Products as Product E-T-15. The resulting product had an acid value of 33.

EXAMPLE 5

Employing the same equipment, temperature conditions, and techniques of Example 1, an amine salt was prepared using 2063 grams (5.0 equivalents (A) of Example A-6 and 1293 grams (5.5 equivalents) of an ethoxylated diamine of the formula $$\text{tallow-N}\begin{array}{c}CH_2CH_2OH\\|\\-CH_2CH_2CH_2N\end{array}\begin{array}{c}CH_2CH_2OH\\CH_2CH_2OH\end{array}$$

available from Akzo Corporation under the same Ethoduomeen T/13.

EXAMPLE 6

Employing the same equipment, temperature conditions, and techniques of Example 1, an amine salt was prepared using 1968 grams (4.0 equivalents Reactant (A) of Example A-8 and 1755 grams (4.5 equivalents) of an ethoxylated diamine of the formula $$\text{tallow-N}\begin{array}{c}(CH_2CH_2O)_xH\\|\\-CH_2CH_2CH_2-N\end{array}\begin{array}{c}(CH_2CH_2O)_yH\\(CH_2CH_2O)_zH\end{array}$$

wherein $x + y + z = 10$ available from Akzo Corporation under the name Ethoduomeen T/20.

EXAMPLE 7

Employing the same equipment, temperature conditions, and techniques of Example 1, an amine salt was prepared using 1298 (2.5 equivalents) Reactant (A) of Example A-3 and 1021 grams (2.7 equivalents) of a propoxylated amine of the formula $$\text{tallow-N}\begin{array}{c}CH_2CHOH\\|\\CH_3\\CH_2CHOH\\|\\CH_3\end{array}$$

available from Akzo corporation under the name Propomeen T/12.

EXAMPLE 8

Employing the same equipment, temperature conditions, and techniques of Example 1, an amine salt was prepared using 917 grams (2.5 equivalents) Reactant (A) of Example A-2 and 2390 grams (2.7 equivalents) of an ethoxylated amine of the formula $$\text{coco-N}\begin{array}{c}(CH_2CH_2O)_xH\\(CH_2CH_2O)_yH\end{array} \quad \text{wherein } x + y = 15$$

available from Sherex Chemicals under the name Varonic K215.

EXAMPLE 9

Employing the same equipment, temperature conditions, and techniques of Example 1, an amine salt was prepared using 1247 grams (2.4 equivalents) Reactant (A) of Example A-3 and 1287 grams (2.6 equivalents) of an ethoxylated amine of the formula

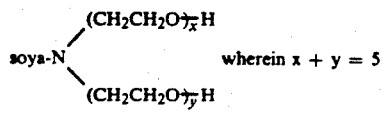

wherein $x + y = 5$ available from Sherex Chemicals under the name Varonic L205.

EXAMPLE 10

Employing the same equipment, temperature conditions, and techniques of Example 1, an amine salt was prepared using 1368 grams (2.0 equivalents) Reactant (A) of Example A-4 and 781 grams (2.2 equivalents) of an ethoxylated amine of the formula

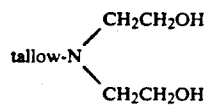

available from Sherex Chemicals under the name Varonic T202.

EXAMPLE 11

Employing the same equipment, temperature conditions, and techniques of Example 1, an amine salt was prepared using 825 grams (2.0 equivalents) Reactant (A) of A-6 and 2057 grams (2.2 equivalents) of an ethoxylated amine of the formula

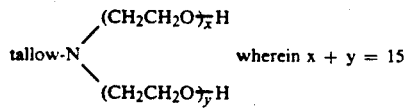

wherein $x + y = 15$ available from Sherex Chemicals under the name Varonic T215.

As previously indicated, the amine salt compositions of this invention are useful as additives in metalworking operations. The compositions were evaluated using bench scale equipment and procedures which are accepted in the metalworking industry as giving results indicative of actual lubricant performance in heavy-duty situations requiring additives that provide EP, anti-friction and anti-wear properties.

Specifically, compositions of this invention were evaluated in the Shell Four-Ball Tester and the Draw Bead Stamping Lubricant Tester (SLT).

The Four-Ball Wear Tester is designed to measure the protection a lubricant additive affords under conditions of high unit pressures and moderate sliding velocities. The test consists of four one-half inch diameter steel balls arranged in the form of an equilateral tetrahedron. The three lower balls are held immovably in a clamping pot to form a cradle in which the fourth ball is caused to rotate about a vertical axis. The lubricant containing the additive under test is held in the clamping pot and covers the areas of control of the four balls. During testing, scars are formed in the surfaces of the three stationary balls. The diameter of the scars is a function of the usefulness of the lubricant additive, i.e., the smaller the scar, the letter the additive.

The compositions of this invention were evaluated in both oil and emulsion. In an oil environment, 5 percent of the compositions of this invention were blended into 95 percent of a 100 neutral oil.

In an emulsion environment, a "soluble oil" was first made utilizing 17 percent of the compositions of this invention, 15 percent Base 8000, 1 percent triethanolamine and 82.3 percent 100 neutral oil. Base 8000 is a product available from Ferro Corporation. The main component of Base 8000 is a sodium salt of a petroleum sulfonic acid. From the soluble oil a soluble oil emulsion was made by mixing 10 percent soluble oil with 90 percent tap water having an 8 grain hardness.

The oil and emulsion blends of the compositions of this invention were compared to oil and emulsion blends of Products a-f that are considered to be obvious to use in metalworking applications. The products are as follows:

Product a - a medium range normal paraffin wax chlorinated to 58-60 percent;

Product b - example 2 of U.S. Pat. No. 4,575,431;

Product c - an oleyl amine salt of a di-n-octyldithiophosphoric acid;

Product d - a triethanolamine salt of a di-tridecyldithiophosphoric acid;

Product e - an ethylene diamine salt of a di-n-octyldithiophosphoric acid; and

Product f - zinc salt of a dihydrocarbyldithiophosphoric acid.

TABLE II

| | | Four-Ball Test Results | | | | |
| | | Oil Four-Ball | | Emulsion Four-Ball | | Emulsion |
| Sample | Blend Composition | Scar, mm | Coef. Frict. | Scar, mm | Coef. Frict. | Appearance |
| --- | --- | --- | --- | --- | --- | --- |
| 1 | Product of Ex. 1 | 0.39 | 0.068 | 0.67 | 0.069 | Slight Cream Separation |
| 2 | Product of Ex. 2 | 0.65 | 0.088 | 0.82 | 0.073 | Slight Cream Separation |
| 3 | Product of Ex. 3 | 0.46 | 0.049 | 0.70 | 0.097 | No Separation |
| 4 | Product of Ex. 4 | 0.49 | 0.067 | 0.64 | 0.104 | No Separation |
| 5 | Product a | 0.51 | 0.088 | 0.93 | 0.123 | No Separation |
| 6 | Product b | 0.42 | 0.060 | (incompatible in emulsion) | | |
| 7 | Product c | 0.41 | 0.053 | 0.79 | 0.065 | Oil Separation |
| 8 | Product d | 0.52 | 0.063 | 0.73 | 0.107 | No Separation |
| 9 | Product e | 0.60 | 0.068 | (incompatible in emulsion) | | |
| 10 | Product f | 0.33 | 0.073 | 0.77 | 0.084 | No Separation |

The results within Table II indicate an improvement of the compositions of this invention over the standard metalworking compositions.

The Stamping Lubricant Tester (SLT) is a Chrysler-type horizontal simulated draw-bead tester equipped with a computerized data system. This test gives a measure of different drawing compounds relative to their lubricating value in a stamping operation. "SLT numbers", with the lower numbers representing better results, are generated which are considered 90 percent reliable as predictors of drawing lubricant acceptability. These numbers are developed from the measurement of force (in pounds) required to pull a 2"×18" metal strip through a set of fixed bead dies over a distance of 5 inches. Various metals can be used, but the results reported here are for 1¼ galvanized steel.

The SLT compares the compositions of this invention with products considered to be obvious in the metalworking art in emulsion. In an oil-containing concentrate, 20 percent of the compositions of this invention were blended with 33 percent Base DS and 47 percent 100 neutral oil. Base DS is a soluble base for drawing and stamping compounds. It is primarily a combination of sodium petroleum sulfonate, rosin acids, alkanolamine salt and nonionic surfactant. Base DS is manufactured by Ferro Corporation.

In order to test the products within an emulsion environment, 20 percent by volume of the composition of the oil-containing concentrate is diluted with 80 percent by volume tap water.

Blends of the compositions of this invention were compared to blends of Products g and h described below:

Product g - a medium range normal paraffin wax chlorinated to 58-60 percent and

Product h a zinc salt of a di-2-ethylhexyldithiophosphoric acid.

TABLE III

SLT Draw Bead Test for an Emulsion

| Sample | Blend Composition | SLT Numbers |
| --- | --- | --- |
| 1 | Product of Ex. 1 | 218.2 |
| 2 | Product of Ex. 3 | 203.3 |
| 3 | Product g | 357.4 |
| 4 | Product h | 372.6 |

The above results shown that the compositions of this invention are superior to the chlorinated paraffins, Product g, when evaluated in emulsion. A zinc soap, product h, was included since these soaps have been known to give performance results representative of some commercial products.

The compositions of this invention can be added directly to a metalworking fluid. Preferably, however, they are diluted with a substantially inert, normally liquid, organic diluent such as mineral oil to form an additive concentrate. These additive concentrates usually contain from about 5 percent to about 90 percent by weight of the compositions of this invention and may contain, in addition, one or more other additives known in the art or described hereinabove.

While in accordance with the Patent Statutes, the best mode and preferred embodiment has been set forth, the scope of the invention is not limited thereto, but rather by the scope of the attached claims.

What is claimed is:

1. A metal working composition, consisting essentially of: an amine salt blended in an oil, wherein the amine salt comprises the reaction product of
   (A) a dihydrocarbyldithiophosphoric acid of the formula

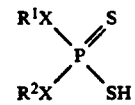

wherein $R^1$ and $R^2$ are hydrocarbyl-based groups independently containing from about 5 to about 30 carbon atoms, X is oxygen or sulfur, and
   (B) an alkoxylated monoamine, diamine, or polyamine, wherein the alkoxylated amine contains from about 5 to about 15 moles of an alkylene oxide.

2. The composition of claim 1, wherein X is oxygen, $R^1$ and $R^2$ are hydrocarbyl groups independently containing from about 5 to about 22 carbon atoms, and (B) is formed from a monoamine of the formula $R^3R^4NH$ wherein $R^3$ is a hydrocarbyl group comprising alkyl or alkenyl containing from about 8 to about 22 carbon atoms, $R^4$ is hydrogen or a hydrocarbyl group containing from about 1 to about 4 carbon atoms, and the alkoxylated amine (B) contains from about 5 up to about 15 moles of an alkylene oxide comprising ethylene oxide or propylene oxide.

3. The composition of claim 2, wherein $R^3$ is an alkyl or alkenyl group containing from about 12 to about 18 carbon atoms, $R^4$ is hydrogen, and the alkoxylated amine (B) contains from about 5 up to about 15 moles ethylene oxide.

4. The composition of claim 3, wherein $R^1$ and $R^2$ are hydrocarbyl groups independently containing from about 6 to about 18 carbon atoms and $R^3$ is an alkyl group containing from about 12 to about 18 carbon atoms.

5. The composition of claim 4, wherein $R^1$ and $R^2$ are both either n-hexyl, n-octyl, tridecyl, or isostearyl groups.

6. The composition of claim 5, wherein the monoamine is ethoxylated to give the structure

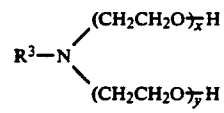

wherein $R^3$ is tallow and the sum of x and y is from about 5 to about 15.

7. The composition of claim 1, wherein X is oxygen, $R^1$ and $R^2$ are hydrocarbyl groups independently containing from about 5 to about 22 carbon atoms, and (B) is formed from a diamine of the formula $R^3NHR^6NH_2$ wherein $R^3$ is a hydrocarbyl group comprising alkyl or alkenyl containing from about 8 to about 22 carbon atoms, $R^6$ comprises —$CH_2$—, —$CH_2CH_2$— or —$CH_2CH_2CH_2$—, and the alkoxylated amine (B) contains from about 5 up to about 15 moles of an alkylene oxide comprising ethylene oxide or propylene oxide.

8. The composition of claim 7, wherein $R^3$ is an alkyl or alkenyl group containing from about 12 to about 18 carbon atoms, $R^6$ is —$CH_2CH_2CH_2$— and the alkoxylated amine (B) contains from about 5 up to about 15 moles ethylene oxide.

9. The composition of claim 8, wherein $R^1$ and $R^2$ are hydrocarbyl groups independently containing from about 6 to about 18 carbon atoms and $R^3$ is an alkyl group.

10. The composition of claim 1, wherein X is oxygen, $R^1$ and $R^2$ are hydrocarbyl groups independently containing from about 5 to about 22 carbon atoms, and (B) is formed from a polyamine of the formula

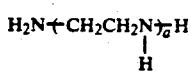

wherein a is an integer of from about 2 to about 10, and the alkoxylated amine (B) contains from about 5 up to about 15 moles of an alkylene oxide comprising ethylene oxide or propylene oxide.

11. The composition of claim 10, wherein $R^1$ and $R^2$ are hydrocarbyl groups independently containing from about 6 to about 18 carbon atoms and a is an integer of from about 2 to about 5.

12. A metal working composition, consisting essentially of:
an amine salt wherein the amine salt comprises the reaction product of
(A) a dihydrocarbyldithiophosphoric acid of the formula

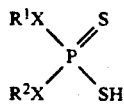

wherein $R^1$ and $R^2$ are hydrocarbyl-based groups independently containing from about 5 to about 30 carbon atoms, X is oxygen or sulfur, and
(B) an alkoxylated monoamine, wherein the alkoxylated monoamine contains from about 5 to about 15 moles of an alkylene oxide.

13. An additive concentrate comprising a substantially inert, normally liquid organic diluent and from about 5 percent to about 90 percent by weight of the composition of claim 12.

14. The composition of claim 12, wherein X is oxygen, $R^1$ and $R^2$ are hydrocarbyl groups independently containing from about 5 to about 22 carbon atoms, and (B) is formed from a monoamine of the formula $R^3R^4NH$ wherein $R^3$ is a hydrocarbyl group comprising alkyl or alkenyl containing from about 8 to about 22 carbon atoms, $R^4$ is hydrogen or a hydrocarbyl group containing from about 1 to about 4 carbon atoms, and the alkoxylated monoamine (B) contains from about 5 up to about 15 moles of an alkylene oxide comprising ethylene oxide or propylene oxide.

15. The composition of claim 14, wherein $R^3$ is an alkyl or alkenyl group containing from about 12 to about 18 carbon atoms, $R^4$ is hydrogen, and the alkoxylated monoamine (B) contains from about 5 up to about 15 moles of ethylene oxide.

16. The composition of claim 15, wherein $R^1$ and $R^2$ are hydrocarbyl groups independently containing from about 6 to about 18 carbon atoms and $R^3$ is an alkyl group containing from about 12 to about 18 carbon atoms.

17. The composition of claim 16, wherein $R^1$ and $R^2$ are both either n-hexyl, n-octyl, tridecyl, or isostearyl groups.

18. The composition of claim 17, wherein the monoamine is ethoxylated to give the structure

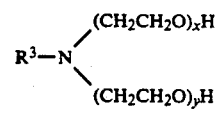

wherein $R^3$ is tallow and the sum of x and y is from about 5 to about 15.

19. An additive concentrate comprising a substantially inert, normally liquid organic diluent and from about 5 percent to about 90 percent by weight of an amine salt, wherein the amine salt comprises the reaction product of
A) a dihydrocarbyldithiophosphoric acid of the formula

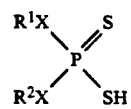

wherein $R^1$ and $R^2$ are hydrocarbyl-based groups independently containing from about 5 to about 30 carbon atoms, X is oxygen or sulfur, and
B) an alkoxylated monoamine, diamine, or polyamine, wherein the alkoxylated amine contains from about 5 to about 15 moles of an alkylene oxide.

* * * * *